US012697465B2

(12) United States Patent
    Rasmussen et al.

(10) Patent No.:  US 12,697,465 B2
(45) Date of Patent:      Aug. 4, 2026

(54) INJECTION MOLDED CANNULA SYSTEM

(71) Applicant: Roche Diabetes Care, Inc.,
               Indianapolis, IN (US)

(72) Inventors: Mads Bjoern Rasmussen, Weinheim
               (DE); Christian Freitag, Weinolsheim
               (DE)

(73) Assignee: Roche Diabetes Care, Inc.,
               Indianapolis, IN (US)

( * ) Notice:   Subject to any disclaimer, the term of this
               patent is extended or adjusted under 35
               U.S.C. 154(b) by 1133 days.

(21) Appl. No.: 17/466,250

(22) Filed:     Sep. 3, 2021

(65)            Prior Publication Data
       US 2021/0393918 A1      Dec. 23, 2021

Related U.S. Application Data

(63) Continuation      of      application      No.
     PCT/EP2020/055766, filed on Mar. 5, 2020.

(30)        Foreign Application Priority Data

Mar. 6, 2019    (EP) ..................................... 19161019

(51) Int. Cl.
     *A61M 25/00*         (2006.01)
     *B29C 45/14*         (2006.01)
     *B29L 31/00*         (2006.01)
(52) U.S. Cl.
     CPC ...  *A61M 25/0014* (2013.01); *B29C 45/14065*
         (2013.01); *B29C 2045/14147* (2013.01); *B29L*
                                  *2031/7548* (2013.01)

(58) Field of Classification Search
     CPC .......... A61M 25/0014; A61M 25/0097; A61M
                              25/0662; B29C 45/14065;
                       (Continued)

(56)            References Cited

U.S. PATENT DOCUMENTS 3,029,815  A     4/1962  Roehr
     3,961,013  A     6/1976  Gütlhuber et al.
                       (Continued)

FOREIGN PATENT DOCUMENTS

DE      35 30 349  C1     4/1987
     EP      3 329 956  A1     6/2018
                       (Continued)

OTHER PUBLICATIONS

International Search Report and Written Opinion of the Interna-
tional Searching Authority, PCT/EP2020/055766, Apr. 9, 2020, 9
pages.

*Primary Examiner* — Bhisma Mehta
*Assistant Examiner* — Haden Matthew Ritchie
(74) *Attorney, Agent, or Firm* — Bose Mckinney & Evans
LLP

(57)            ABSTRACT

Disclosed is a cannula system having a soft cannula and a
cannula unit for holding the soft cannula. The cannula unit
includes a compressor and a body, and the body contains a
mounting structure and a cavity for holding a septum. The
soft cannula is threaded on the mounting structure. Further-
more, the compressor circumferentially surrounds the
mounting structure and at least parts of the body. The
compressor contains an internal material tension for exerting
a compression force on the soft cannula and the mounting
structure.

16 Claims, 2 Drawing Sheets

(58) Field of Classification Search
CPC .... B29C 45/14336; B29C 2045/14147; B29C
45/14467; B29L 2031/7548
See application file for complete search history.

(56) References Cited

U.S. PATENT DOCUMENTS

| | | | |
|---|---|---|---|
| 4,430,081 A | 2/1984 | Timmermans | |
| 4,781,703 A | 11/1988 | Walker et al. | |
| 4,838,873 A | 6/1989 | Landskron et al. | |
| 6,120,480 A | 9/2000 | Zhang et al. | |
| 8,152,758 B2 * | 4/2012 | Chan ..................... | A61M 29/00 |
| | | | 604/96.01 |
| 2006/0079848 A1 | 4/2006 | Pelkey et al. | |
| 2014/0350485 A1 * | 11/2014 | Sonderegger ....... | B29C 45/1657 |
| | | | 604/533 |
| 2017/0135720 A1 | 5/2017 | Oshida et al. | |
| 2019/0160258 A1 * | 5/2019 | Kristen ............. | A61M 25/0014 |
| 2019/0275238 A1 * | 9/2019 | Arnold ............. | A61M 25/0014 |
| 2022/0126019 A1 | 4/2022 | Freitag et al. | |

FOREIGN PATENT DOCUMENTS

| | | |
|---|---|---|
| JP | S 60-144448 U | 9/1985 |
| JP | 2008-504929 A | 2/2008 |
| JP | 2017-086566 A | 5/2017 |
| JP | 2018-166953 A | 11/2018 |
| WO | WO 99/21605 A2 | 5/1999 |
| WO | WO 2006/012281 A1 | 2/2006 |
| WO | WO 2018/033614 A1 | 2/2018 |
| WO | WO 2018/100072 A1 | 6/2018 |

* cited by examiner

Fig. 2a                    Fig. 2b

INJECTION MOLDED CANNULA SYSTEM

RELATED APPLICATIONS

This application is a continuation of PCT/EP2020/ 055766, filed Mar. 5, 2020, which claims priority to EP 19 161 019.5, filed Mar. 6, 2019, the entire disclosures of both of which are hereby incorporated herein by reference.

BACKGROUND

This disclosure lies in the field of infusion technology. More particularly, it is related to infusion site interfaces and infusion pumps, as well as manufacturing methods for cannula systems for infusion site interfaces.

Infusion pumps are used for parenterally providing patients with liquid medicaments over longer time periods. Nowadays, infusion pumps with very small dimensions are available that can be carried by the patient on the body. Such small-sized ambulatory infusion pumps are particularly useful for metering small doses of highly effective liquid medicaments, such as insulin for the treatment of diabetes, or analgesics for pain therapy, which are conveyed through a cannula into the tissue of a patient.

In one approach, an infusion pump, carried somewhere on the body, e.g., attached to a belt, is fluidly connected via flexible tubing to an infusion site interface, also called insertion head, that is attached to the body of the patient. The infusion site interface comprises a cannula system with a cannula to be inserted into the body tissue, a housing, and a connector for fluidly connecting the cannula with the flexible tubing connected to the upstream infusion pump. The tubing can be repeatedly connected and disconnected from the infusion site interface. The connector may for example include a septum sealingly closing the fluid system of cannula and housing. The septum can be penetrated by a hollow needle for reversibly establishing a fluid connection. The cannula is preferably made of a flexible material and is generally a soft cannula. Such cannulas are more comfortable for their users, particularly during body movements. Since flexible cannulas typically cannot be inserted directly into the tissue, an additional piercing device, e.g., in the form of a rigid piercing needle made from metal, is arranged inside the flexible cannula. A pointed end of the piercing device protrudes from the proximal end of the cannula, the cannula that will be open toward the interstitial fluid. After inserting the piercing device and the stabilized cannula into the body tissue, the rigid piercing device is removed from the flexible cannula. The cannula remains in the body tissue. Generally, a piercing needle is arranged in such a way that it penetrates a septum, which after withdrawal of the piercing needle sealingly closes the distal end of the now open cannula fluid path.

In another approach, the infusion pump device is directly fluidly connected with the infusion site interface. The fluid connection between pump and cannula is established by a hollow connector needle of the pump, reversibly penetrating a septum of the cannula unit that sealingly closes the distal end of the cannula fluid path. Advantageously, the pump can be repeatedly connected and disconnected from the infusion site interface.

In a common method for manufacturing infusion site interfaces with soft and flexible cannulas, a stabilizing pin is introduced in a first step into the flexible cannula, for simplifying the handling of the flexible cannula during the manufacturing process. The temporary structural unit prepared in this manner is inserted into a previously manufactured housing, the flexible cannula and the housing are permanently connected, for example by a thermal process. The stabilizing pin is then drawn out of the flexible cannula, and is replaced by the actual piercing device. The insertion of the piercing devices sometimes damages the flexible cannulas, which results in comparably high rejection rates during manufacturing.

WO 2018 033 614 A1 discloses a cannula unit comprising a housing and a flexible cannula. The flexible cannula is provided with an end area that deviates from the shape of the rest of the flexible cannula. The end area of the flexible cannula has for example a funnel-like shape or the shape of the flange. Furthermore, the housing comprises two parts, between which the end area of the flexible cannula is positively locked to the housing by clamping. The two parts of the housing are ultimately connected by welding, particularly laser welding.

Cannula units and systems known in the state of the art suffer from certain drawbacks. For example, if the cannula unit has a housing with two parts, which are separately produced and only subsequently connected during the manufacturing process, certain restrictions are imposed. Firstly, the materials have to be suitable for welding or gluing, such that the two housing parts can be connected. Secondly, the connecting step represents an additional step, which increases the manufacturing time and cost of the production. Thirdly, the two parts of the housing must be strictly complementary to each other, thus allowing only minor material tolerances, as otherwise leakage becomes a problem. This is a severe problem in the state of the art, as the amount of deficient products due to non-complementary housing parts is significantly high.

SUMMARY

This disclosure improves the state of the art regarding the design and use of cannula systems in the context of infusion of liquid drugs, thereby preferably avoiding disadvantages of the prior art fully or partly.

In advantageous embodiments, a cannula unit is provided, in which the occurrence of leakage is avoided or at least significantly reduced.

In further favorable embodiments, a cannula unit is provided, which can be manufactured in a time and cost efficient manner.

In additional favorable embodiments, the amount of deficient products during the manufacturing process and thus the rejection rate is reduced.

According to a first aspect, a method for manufacturing a cannula system with a body unit and a compressing unit is disclosed. The method comprises providing the body unit comprising a mounting structure, the body unit being mounted onto a molding core pin. Subsequently, a soft cannula is threaded on the mounting structure of the body unit. In a following step, the compressing unit is injection molded on the soft cannula and at least on parts of the body unit. The compressing unit circumferentially surrounds the mounting structure, at least parts of the soft cannula and at least parts of the body unit. Furthermore, the injection-molded compressing unit is cooled, thereby providing an internal material tension of the compressing unit. The cooling typically entails shrinking of the compressing unit. In addition, the molding core pin is removed. It is understood by the skilled person that the molding core pin can be removed either directly after injection molding of the compressing unit, i.e., before cooling of the compressing unit, after cooling the compressing unit or even during cooling of the compressing unit.

The body unit is preferably also produced by injection molding. For example, the body may be provided by injection molding onto the molding core pin. However, the body unit may also be produced by another suitable method. Particularly, if the body unit is produced by injection molding, the two injection molding steps may be conducted as two separate injection molding steps.

Using injection-molding technology for manufacturing the compressing unit and optionally the body unit has the advantage that only a reduced number of tools is required. Furthermore, no additional connection step such as welding or gluing, is required. In addition, as the compressing unit is injection molded on the body unit and the cannula and subsequently cooled, shrinking induces an internal material tension, which significantly increases the fixture of the soft cannula within the cannula system. The shrinking and the thus associated internal material tension can be increased, if cooling is performed in the mold. Furthermore, injection molding of both the body unit and the compressing unit has the advantage that the two parts are necessarily complementary to each other and thus the amount of material deficient parts is significantly reduced.

It is understood that the term "circumferentially" does not necessarily require that the mounting structure, the cannula and or the body unit have a round cross section and/or a cylindrical shape. These components may independently of each other comprise a round, elliptical or angular cross section and further have any shape suitable for an infusion set.

In some embodiments the compressing unit is injection molded such that it circumferentially surrounds at least ⅓, preferably ½ of the outer surface of the body unit, thereby providing a particular tight and safe connection between the body unit and the compressing unit.

In further embodiments, only a distal end area of the soft cannula is threaded on the mounting structure of the body unit. The compressing unit preferably circumferentially surrounds only the distal end area of the soft cannula. As the skilled person understands, the distal end area is facing away from the patient in an operative state. Thus, the distal end area is closer to the body unit than the proximal end area. Upon insertion into the patient's tissue, the proximal end area is therefore first inserted into the tissue.

In other embodiments, the distal end area of the soft cannula has a larger diameter than the rest of the cannula before the cannula is threaded on the mounting structure. Thus, the cannula is, when pushed over the mounting structure, only slightly laterally expanded or not at all, which will result in little if any material creep and potentially leads to less leakage.

In further embodiments, the internal material tension of the compressing unit exerts a compression force which is directed radially inwards. Such a force is particularly advantageous, as the risk of leakage between the cannula and the mounting structure and/or between the cannula and the compressing unit is further decreased.

In other embodiments, the internal material tension of the compressing unit compresses the parts of the soft cannula threaded on the mounting structure. In such embodiments, at least the part of the cannula which is circumferentially surrounded by the compressing unit, preferably the distal end area, is compressed. Thus, the wall thickness of the cannula of this part is smaller than the wall thickness of the rest of the cannula which is not circumferentially surrounded by the compressing unit.

In further embodiments, the body unit and the compressing unit and/or the compressing unit and the soft cannula form a bonded connection during injection molding of the compressing unit.

In other embodiments, the methods consists of two separate injection molding steps, thereby reducing the required amount of manufacturing steps and the overall production time and costs even further.

According to a second aspect, a cannula system is provided comprising a soft cannula and a cannula unit for holding the soft cannula. The cannula unit comprises or alternatively may also consist of a compressing unit and a body unit, wherein the body unit contains a mounting structure and a cavity for holding a septum. The soft cannula is threaded on the mounting structure of the body unit. Furthermore, the compressing unit circumferentially surrounds the mounting structure and at least parts of the body unit. The compressing unit also comprises an internal material tension for exerting a compression force on the soft cannula and the mounting structure.

For example, such a cannula system may be manufactured by a method as described herein. Furthermore, the body unit and/or the compressing unit are typically injection molded.

In some embodiments, the mounting structure may be a protuberance, in particular a cylindrical or cubical protuberance.

In further embodiments, only a distal end area of the soft cannula is threaded on the mounting structure and the compressing unit circumferentially surrounds the distal end area of the soft cannula.

In other embodiments, the distal end area of the soft cannula has a larger diameter than the rest of the soft cannula. Thus, in these embodiments, the whole distal area has a larger diameter than the rest of the soft cannula.

Typically, the distal end area of the soft cannula is free of an internal material tension.

In some embodiments, the wall thickness of the distal end area of the soft cannula is smaller than the wall thickness of the rest of the soft cannula.

In other embodiments, the compressing unit compresses at least the distal end area of the soft cannula. In these embodiments, a particular fluid tight system is achieved and the risk of leakage is reduced.

In further embodiments, the body unit and the compressing unit are connected by a bonded connection and/or the soft cannula and the compressing unit are connected by a bonded connection.

It is understood that such a bonded connection is typically only formed by the body unit, the compressing unit and/or the soft cannula itself. Thus an external adhesive, for example a glue, is neither required nor present.

In some embodiments, the cannula system does not comprise additional connection means, particularly form-lock means, for coupling and/or connecting the compressing unit and the body unit such as for example barbs, nipples, snap fits and the like.

In further embodiments, the body unit may comprise a septum within the cavity for holding the septum. The septum may be fixed by crimping. Such a septum is typically free of a slit prior to insertion of a piercing needle. In particular, such a septum may not comprise a slit elongated in both the lateral and the vertical piercing direction of the septum.

According to another aspect, a cannula system according to any of the embodiments described herein is used in an infusion set.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIGS. 2a to 2c schematically show the manufacturing method of a cannula system according to an embodiment.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
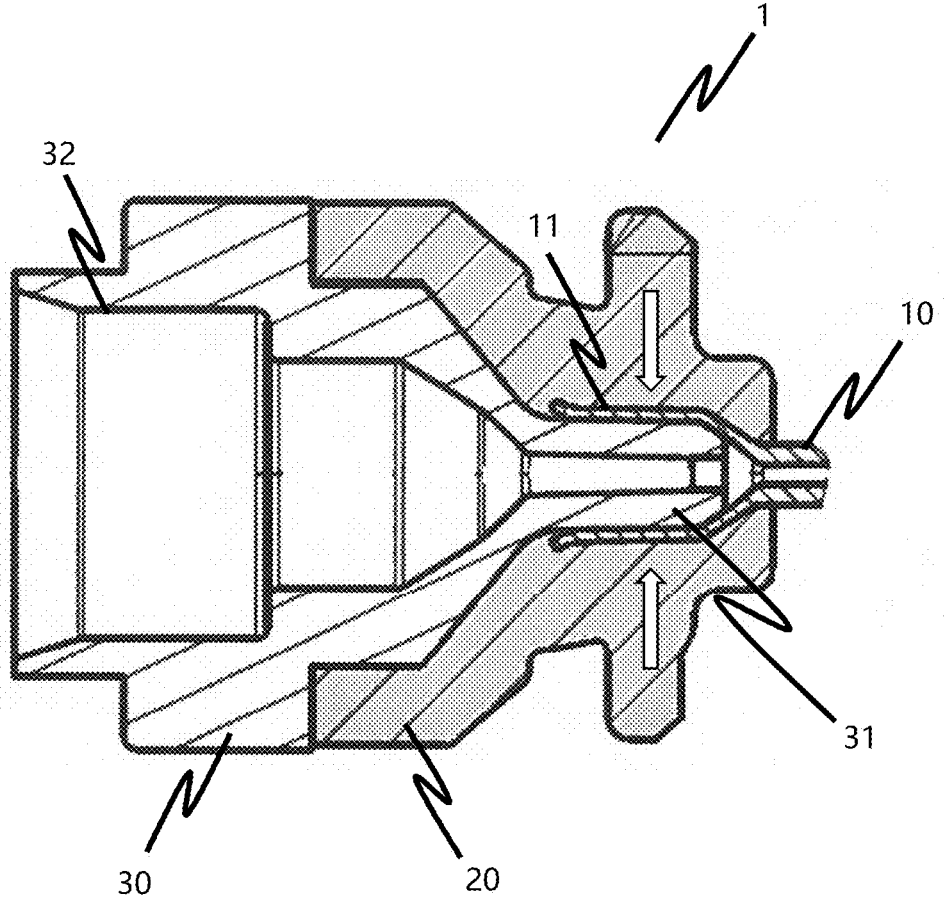
FIG. 1 shows a cross-sectional view of a cannula system in accordance with an embodiment.

FIG. 1 shows an advantageous embodiment of a cannula system 1. Cannula system 1 comprises soft cannula 10 and a cannula unit for holding soft cannula 10. The cannula unit comprises compressing unit 20 (also referred to herein as a "compressor") and body unit 30 (also referred to herein as "body"). Body unit 30 further comprises mounting structure 31 (also referred to herein as "mount") and cavity 32 for receiving a septum. Distal part 11 of soft cannula 10 is threaded on mounting structure 31. The diameter of distal end area 11 of soft cannula 10 is larger than the diameter of the rest of the soft cannula. Compressing unit 20 circumferentially surrounds distal end area 11 of soft cannula 10, mounting structure 31 and also an additional part of body unit 30. As shown in FIG. 1, more than ⅓ of the surface of the body unit is circumferentially surrounded by compressing unit 20.

As indicated by the arrows, the compressing unit 20 has an internal material tension, thereby exerting a radially inwards directed compression force on the distal end area of the soft cannula and the mounting structure. As a result, a particular tight connection between soft cannula 10, mounting structure 31 and compressing unit 20 is achieved. Furthermore, as can be readily seen in FIG. 1, the wall thickness of distal end area 11 of soft cannula 10 is smaller than the wall thickness of the rest of soft cannula 10. In addition, as indicated by the arrows, distal end area 11 of soft cannula 10 is compressed by the compression force exerted by compressing unit 20. Compressing unit 20 and body unit 30 are connected by a bonding connection at their contact area. As a result, a reliable and sealingly tight connection is established.

Figure 2C:
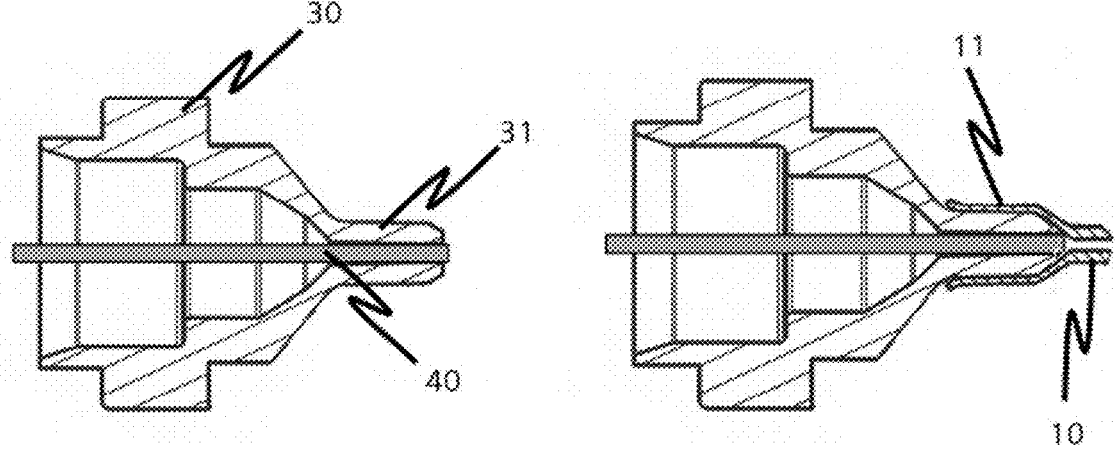
Figure 2C:
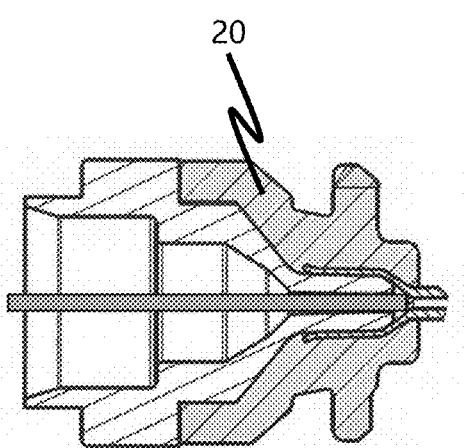

FIGS. 2a to 2c depict certain steps of a method of manufacturing a cannula system according to an advantageous embodiment of this disclosure. As shown in FIG. 2a, body unit 30 with mounting structure 31 is injection molded onto a molding core pin 40 (mold not shown). In a following step, distal end area 11 of soft cannula 10 is threaded on mounting structure 31 (FIG. 2b). Afterwards, compressing unit 20 is injection molded on the distal end area of the soft cannula, on the mounting structure and also on further parts of body unit 30 (FIG. 2c, mold not shown). As the compressing unit is at least partially injection molded on body unit 30, any production imprecision of the proximal face of the body unit is less relevant, as the compressing unit is necessarily complementary to those parts of the body unit 30. Once compressing unit has been injection molded, molding core pin 40 can be removed and the compressing unit be cooled, upon which an internal material tension is established, thereby exerting a force on distal end area 11 of soft cannula 10 and mounting structure 31. Generally, the cooling can be performed in the mold and/or the cooling may be achieved by active cooling. Thus, the compressing unit is not allowed to cool to room temperature by itself, but actively cooled, particularly by using a cooling medium. Such rapid cooling enhances the internal material tension. The two-step injection molding sequence can be performed significantly faster as the methods for manufacturing cannula unit as known in the state of the art.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method for manufacturing a cannula system, comprising:

providing a body having a mounting structure, the body being mounted onto a molding core pin;

threading a soft cannula on the mounting structure of the body;

injection molding a compressor on the soft cannula and at least part of the body, wherein the compressor circumferentially surrounds the mounting structure, at least part of the soft cannula and at least part of the body whereby the compressor forms a bonded connection with the at least part of the soft cannula and the at least part of the body;

cooling the compressor to thereby provide an internal material tension of the compressor; and removing the molding core pin.

2. The method according to claim 1, wherein the body is injection molded onto the molding core pin.

3. The method according to claim 1, wherein only a distal end area of the soft cannula is threaded on the mounting structure, and wherein the compressor circumferentially surrounds only the distal end area of the soft cannula.

4. The method according to claim 3, wherein the distal end area of the soft cannula has a larger diameter than the remainder of the cannula before the cannula is threaded on the mounting structure.

5. The method according to claim 1, wherein the internal material tension of the compressor exerts a radially inwardly directed compression force.

6. The method according to claim 1, wherein the internal material tension of the compressor compresses the soft cannula.

7. The method according to claim 1, wherein the method includes two separate injection molding steps.

8. The method according to claim 1, wherein the bonded connection between the compressor and the at least part of the soft cannula is the sole means of connection between the compressor and the soft cannula and wherein the bonded connection between the compressor and the at least part of the body is the sole means of connection between the compressor and the body.

9. The method according to claim 1, wherein:

the bonded connection between the compressor and the at least part of the soft cannula is an adhesive-free connection and forms the sole means of connection between the compressor and the soft cannula;

wherein the bonded connection between the compressor and the at least part of the body is an adhesive-free connection and forms the sole means of connection between the compressor and the body and the bonded connection between the compressor and the body forms a sealingly tight connection; and wherein the compressor exerts a compression force which is directed radially inwardly whereby the soft cannula has a first wall thickness and a second wall thickness, the first wall thickness being defined by the at least part of the soft cannula surrounded by the compressor and being smaller than the second wall thickness which is defined by a remainder of the soft cannula.

10. A cannula system, comprising:

a soft cannula; and a cannula assembly for holding the soft cannula, wherein the cannula assembly comprises a compressor and a body and wherein the body further comprises a mounting structure and a cavity configured to hold a septum;

wherein, the soft cannula is threaded onto the mounting structure and the compressor circumferentially surrounds the mounting structure and at least part of the body;

wherein, the compressor comprises an internal material tension configured for exerting a compression force on the soft cannula and the mounting structure; and wherein the body and the compressor are connected by a bonded connection formed by injection molding the compressor on the at least part of the body and wherein the soft cannula and the compressor are connected by a bonded connection formed by injection molding the compressor on the soft cannula where the compressor circumferentially surrounds the mounting structure.

11. The cannula system according to claim 10, wherein only a distal end area of the soft cannula is threaded on the mounting structure, and wherein the compressor circumferentially surrounds the distal end area of the soft cannula.

12. The cannula system according to claim 11, wherein distal end area of the soft cannula has a larger diameter than the remainder of the soft cannula.

13. The cannula system according to claim 11, wherein the compressor compresses at least the distal end area of the soft cannula.

14. The cannula system according to claim 10, wherein the bonded connection between the compressor and the body is the sole means of connection between the compressor and the body, and wherein the bonded connection between the compressor and the soft cannula is the sole means of connection between the compressor and the soft cannula.

15. The cannula system according to claim 14, wherein the bonded connection between the compressor and the body forms a sealingly tight connection.

16. The cannula system according to claim 10, wherein:

the bonded connection between the compressor and the at least part of the soft cannula is an adhesive-free connection and forms the sole means of connection between the compressor and the soft cannula;

wherein the bonded connection between the compressor and the at least part of the body is an adhesive-free connection and forms the sole means of connection between the compressor and the body and the bonded connection between the compressor and the body forms a sealingly tight connection; and wherein the compressor exerts a compression force which is directed radially inwardly whereby the soft cannula has a first wall thickness and a second wall thickness, the first wall thickness being defined by the at least part of the soft cannula surrounded by the compressor and being smaller than the second wall thickness which is defined by a remainder of the soft cannula.

* * * * *